United States Patent [19]

Stephens

[11] 4,259,068

[45] Mar. 31, 1981

[54] ORAL RETRACTOR

[76] Inventor: Dennis B. Stephens, 15171 El Rancho Ave., Visalia, Calif. 93277

[21] Appl. No.: 49,213

[22] Filed: Jun. 18, 1979

[51] Int. Cl.³ ............................................... A61C 5/00
[52] U.S. Cl. ...................................................... 433/140
[58] Field of Search ................. 128/12, 13, 14, 15; 433/140, 137

[56] References Cited

U.S. PATENT DOCUMENTS

| | | | |
|---|---|---|---|
| 160,604 | 3/1875 | Lewis | 433/137 |
| 1,400,854 | 12/1921 | Barr | 128/15 |

*Primary Examiner*—Robert Peshock
*Attorney, Agent, or Firm*—Dennis B. Haase

[57] ABSTRACT

The present invention relates to retractors generally, and more specifically to oral retractors for use in conjunction with the administration of anesthesia, as well as for use in conjunction with the performance of other surgical and dental procedures.

More specifically, the invention comprises a flat metal strip having one end thereof formed into a tapered hook for insertion into the patient's mouth. The strip is bent or formed intermediate its ends so as to cause the end remote from the hook to project downwardly and in an essentially parallel relation with respect to the tapered hook end. A weight is secured to the end remote from the hook, whereby the lips are retracted upon placement of the instrument properly in the patient's mouth to thereby permit the physician to work in the area proximate the hook without interference from the patient's lip or from the instrument itself.

1 Claim, 4 Drawing Figures

U.S. Patent        Mar. 31, 1981        4,259,068
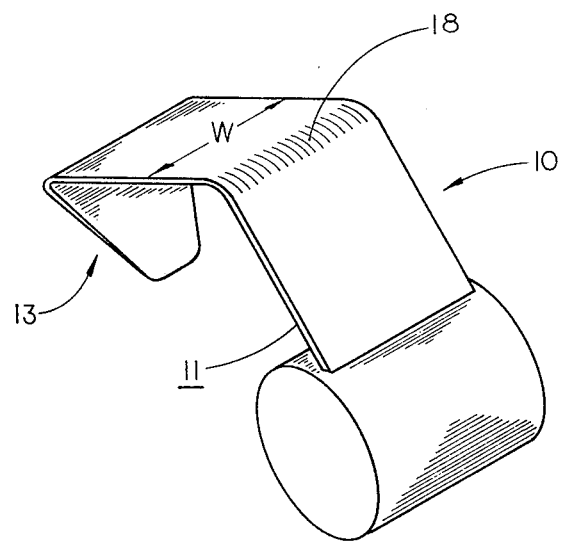
FIG. 1
FIG. 3
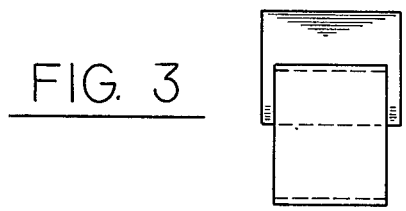
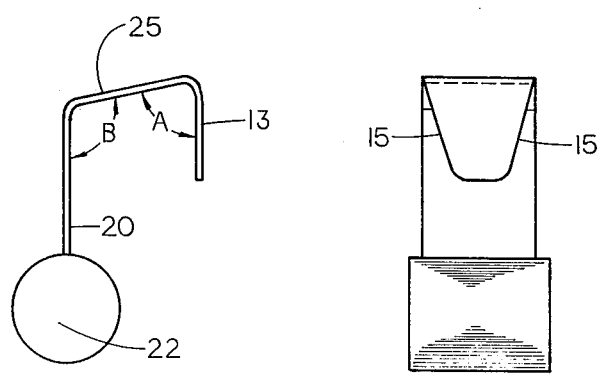
FIG. 2        FIG. 4

ORAL RETRACTOR

BACKGROUND OF THE INVENTION

Specula and retractors of various types and configurations are currently in use primarily in the medical field to mechanically retract or pull aside tissue or skin from an opening or incision through which a physician or dentist is attempting to work. The purpose of the retractor is to permit the physician or dentist free and unhampered access to the work area without necessity of having to physically hold a particular tissue area away which would result in a diversion of the physician's attention to his task.

Little attention has been given, however, to those who are required to work in the mouth. Often the mouth area is quite small and the area to which the physician must direct his attention is quite difficult to reach. The problems with retracting the lip areas are experienced not only by oral surgeons, but by anesthesiologists who must work in the area. Furthermore, because of the muscle tissue around the mouth and cheek areas, conventional retractor designs currently in use are ill-suited to the task. The present invention, however, was developed specifically for use in conjunction with oral procedures and provides the user with a novel and heretofore unavailable instrument capable of retracting the lip area to permit the physician to work in the area of the mouth unhampered by the unwillingness or inability of the patient to effectively assist the physician by proper retraction of the lip.

BRIEF DESCRIPTION OF THE DRAWING

Having thus described the invention, and the environment within which it is intended to function, there is presented concurrently herewith a sheet of drawings illustrating various aspects of the invention, wherein:

FIG. 1 is a perspective view of a retractor constructed in accordance with the present invention;

FIG. 2 is a side elevation of the retractor illustrating the relative location of the various elements thereof;

FIG. 3 is a top plan view of the retractor of FIG. 1; and

FIG. 4 is a rear elevation illustrating the tapered hook in relation to various other elements of the invention.

DESCRIPTION OF THE PREFERRED EMBODIMENT

With reference now to the drawings, and particularly with respect to FIG. 1, there is illustrated an oral retractor at 10 which is constructed in accordance with the present invention. The retractor comprises a flat metal strip 11 having a hook portion 13 formed at one end thereof. As may be seen particularly in FIGS. 1 and 4, the sides 15 of the hooked end are tapered inwardly so as to minimize any discomfort which the patient might experience by having the retractor in position.

The flat metal strip is formed at 18 so as to align the hooked end 13, and the end 20 remote therefrom in parallel. Retraction force is provided by a cylindrical weight 22 affixed to the remote end 20 in a suitable fashion.

It has been found that a width W of approximately one inch provides a satisfactory retraction capability while at the same time minimizing the discomfort to the patient himself. Likewise, the length of the hook end fits, in satisfactory fashion in most mouths, including those of infants, at a length of approximately one inch.

In order that the instrument will be effective, while at the same time being out of the way of the physician, it must depend from the mouth so as to provide optimum retraction without unnecessary protrusion or extension from the work area. The retractor of the present invention is particularly adapted for this purpose, therefore, by providing an included angle between the hooked end and that portion of the metal strip 25 which is contiguous with the hooked end 13 of approximately 85°. The deformation 18 has been found to be most satisfactory at an included angle B of 105°. These angles provide optimum workability by permitting the hooked end 13 to fit into the mouth and retract the lip with the retractor in close proximity to the facial and cheek muscles with the weight depending directly downward to provide optimum retraction with minimum discomfort.

Having thus described my invention, what is claimed is:

1. Flat metal strip of unilateral construction, hook shaped end having tapered edges adapted to be inserted the mouth of a patient in engagement with the lip thereof while said patient is in a prone position said strip being bent intermediate the ends thereof in such fashion as to bring the hooked end and the end remote therefrom into approximate parallel alignment, and means defining a weight secured to said remote end and having mass sufficient to cause retraction of the lip when said hook end is placed in the patient's mouth.

* * * * *